(12) United States Patent
Stubbs

(10) Patent No.: US 7,354,391 B2
(45) Date of Patent: Apr. 8, 2008

(54) IMPLANTABLE RADIOTHERAPY/BRACHYTHERAPY RADIATION DETECTING APPARATUS AND METHODS

(75) Inventor: James B. Stubbs, Alpharetta, GA (US)

(73) Assignee: Cytyc Corporation, Marlborough, MA (US)

( * ) Notice: Subject to any disclaimer, the term of this patent is extended or adjusted under 35 U.S.C. 154(b) by 458 days.

(21) Appl. No.: 10/704,340

(22) Filed: Nov. 7, 2003

(65) Prior Publication Data

US 2005/0101824 A1  May 12, 2005

(51) Int. Cl.
*A61N 5/00* (2006.01)
(52) U.S. Cl. .......................................................... 600/3
(58) Field of Classification Search ................ 600/1–8
See application file for complete search history.

(56) References Cited

U.S. PATENT DOCUMENTS

| | | | |
|---|---|---|---|
| 3,324,847 A | 6/1967 | Zoumboulis | 128/1.2 |
| 3,872,856 A | 3/1975 | Clayton | 128/1.2 |
| 4,417,576 A | 11/1983 | Baran | 128/207.15 |
| 4,706,652 A | 11/1987 | Horowitz | 128/1.2 |
| 4,754,745 A | 7/1988 | Horowitz | 128/1.2 |
| 4,763,642 A | 8/1988 | Horowitz | 128/1.2 |
| 4,821,725 A | 4/1989 | Azam et al. | 128/420 A |
| 4,867,741 A | 9/1989 | Portnoy | 604/10 |
| 5,030,195 A | 7/1991 | Nardi | 600/7 |
| 5,084,001 A | 1/1992 | Van't Hooft et al. | 600/3 |
| 5,084,015 A | 1/1992 | Moriuchi | 604/96 |
| 5,106,360 A | 4/1992 | Ishiwara et al. | 600/2 |
| 5,112,303 A | 5/1992 | Pudenz et al. | 604/49 |
| 5,152,747 A | 10/1992 | Olivier | 604/93 |
| 5,236,410 A | 8/1993 | Granov et al. | 600/12 |
| 5,429,582 A | 7/1995 | Williams | 600/2 |
| 5,484,384 A | 1/1996 | Fearnot | 600/3 |
| 5,503,613 A | 4/1996 | Weinberger | 600/3 |
| 5,566,221 A | 10/1996 | Smith et al. | 378/145 |
| 5,611,767 A | 3/1997 | Williams | 600/2 |
| 5,662,580 A | 9/1997 | Bradshaw et al. | 600/3 |
| 5,707,332 A | 1/1998 | Weinberger | 600/3 |

(Continued)

FOREIGN PATENT DOCUMENTS

EP  0340881  11/1989

(Continued)

OTHER PUBLICATIONS

Ashpole, R.D. et al., "A New Technique of Brachytherapy for Malignant Gliomas with Caesium-137: A New Method Utilizing a Remote Afterloading System," Clinical Oncology, vol. 2, 333-7 (1990).

(Continued)

*Primary Examiner*—John P Lacyk
(74) *Attorney, Agent, or Firm*—Heather Larson; Mark J. Casey

(57) ABSTRACT

An interstitial brachytherapy apparatus and method for delivering and monitoring radioactive emissions delivered to tissue surrounding a resected tissue cavity. The brachytherapy device including a catheter body member having a proximal end, a distal end, and an outer spatial volume disposed proximate to the distal end of the body member. A radiation source is disposed in the outer spatial volume and a treatment feedback sensor is provided on the device. In use, the treatment feedback sensor can measure the radiation dose delivered from the radiation source.

28 Claims, 4 Drawing Sheets

U.S. PATENT DOCUMENTS

| | | | |
|---|---|---|---|
| 5,713,828 A | 2/1998 | Coniglione | 600/7 |
| 5,720,717 A | 2/1998 | D'Andrea | 604/21 |
| 5,764,723 A | 6/1998 | Weinberger et al. | 378/65 |
| 5,782,742 A | 7/1998 | Crocker et al. | 600/3 |
| 5,785,688 A | 7/1998 | Joshi et al. | 604/141 |
| 5,993,374 A | 11/1999 | Kick | 600/8 |
| 6,036,631 A | 3/2000 | McGrath et al. | 600/3 |
| 6,048,299 A | 4/2000 | Hoffmann | 600/3 |
| 6,120,523 A | 9/2000 | Crocker et al. | 606/192 |
| 6,149,574 A | 11/2000 | Trauthen et al. | 600/3 |
| 6,149,575 A * | 11/2000 | Leonhardt | 600/4 |
| 6,176,821 B1 | 1/2001 | Crocker et al. | 600/3 |
| 6,251,059 B1 | 6/2001 | Apple et al. | |
| 6,261,320 B1 | 7/2001 | Tam et al. | 623/1.15 |
| 6,287,249 B1 | 9/2001 | Tam et al. | 600/3 |
| 6,320,935 B1 | 11/2001 | Shinar et al. | |
| 6,402,689 B1 | 6/2002 | Scarantino et al. | |
| 6,413,204 B1 | 7/2002 | Winkler et al. | |
| 6,419,692 B1 | 7/2002 | Yang et al. | 623/1.15 |
| 6,458,069 B1 | 10/2002 | Tam et al. | 600/3 |
| 6,471,630 B1 | 10/2002 | Sioshansi et al. | 600/1 |
| 6,487,438 B1 | 11/2002 | Widmark et al. | 600/431 |
| 6,746,465 B2 * | 6/2004 | Diederich et al. | 606/192 |
| 2003/0028097 A1 | 2/2003 | D'Amico et al. | 600/427 |
| 2003/0114878 A1 | 6/2003 | Diederich et al. | 606/192 |
| 2003/0163016 A1 | 8/2003 | Testardi | |
| 2004/0006305 A1 * | 1/2004 | Hebert et al. | 604/96.01 |

FOREIGN PATENT DOCUMENTS

| | | |
|---|---|---|
| EP | 0867200 | 9/1998 |
| EP | 1 316330 A1 | 6/2003 |
| GB | 2105201 | 3/1983 |
| WO | 9210932 | 7/1992 |
| WO | 9309724 | 5/1993 |
| WO | 9719723 | 6/1997 |
| WO | 9812979 | 4/1998 |
| WO | 9911325 | 3/1999 |
| WO | 9933515 | 7/1999 |
| WO | 9942163 | 8/1999 |
| WO | WO 03/062855 A1 | 7/2003 |

OTHER PUBLICATIONS

A. Bex et al., "A System For Focal Intracavitary Irradiation Of Bladder Cancer With Remote Iridium-192 Afterloading", 21 Eur Urol 1992, 245-249 (1992).

Chun, M. etal. "Interstitial Iridium-192 Implantation for Malignant Brain Tumours. Part II: Clinical Experience," *The British Journal of Radiology*, vol. 62, 158-62 (1989).

Garfield, J. et al., "Postoperative Intracavitary Chemotherapy of Malignant Gliomas," *J. Neurosurg.*, vol. 39, 315-22 (Sep. 1973).

Gutin, P. et al., "Brachytherapy of Recurrent Malignant Brain Tumors With Removable High-Activity Iodine-125 Sources," *J. Neurosurg.*, vol. 60, 61-8 (1984).

Johannesen, T.B. et al., "Intracavity Fractionated Balloon Brachytherapy in Glioblastroma," *Acta Neurochir (Wien)*, vol. 141, 127-33 (1999).

Leibel, S. et al., "The Integration of Interstitial Implantation Into the Preliminary Management of Patients With Malignant Gliomas: Results of a Phase II Northern California Oncology Group Trial," *Am. J. Clin. Oncol. (CCT)*, vol. 10, No. 2, p. 106 (1987).

Roberts, D. et al., "Interstitial Hyperthermia and Iridium Brachytherapy in Treatment of Malignant Glioma," *J. Neurosurg.*, vol. 64, 581-7 (1986).

Wu, A. et al., "Interstitial Iridium-192 Implantation for Malignant Brian Tumours. Part 1: Techniques of Dosimetry Planning," *The British Journal of Radiology*, vol. 62, 154-7 (1989).

* cited by examiner

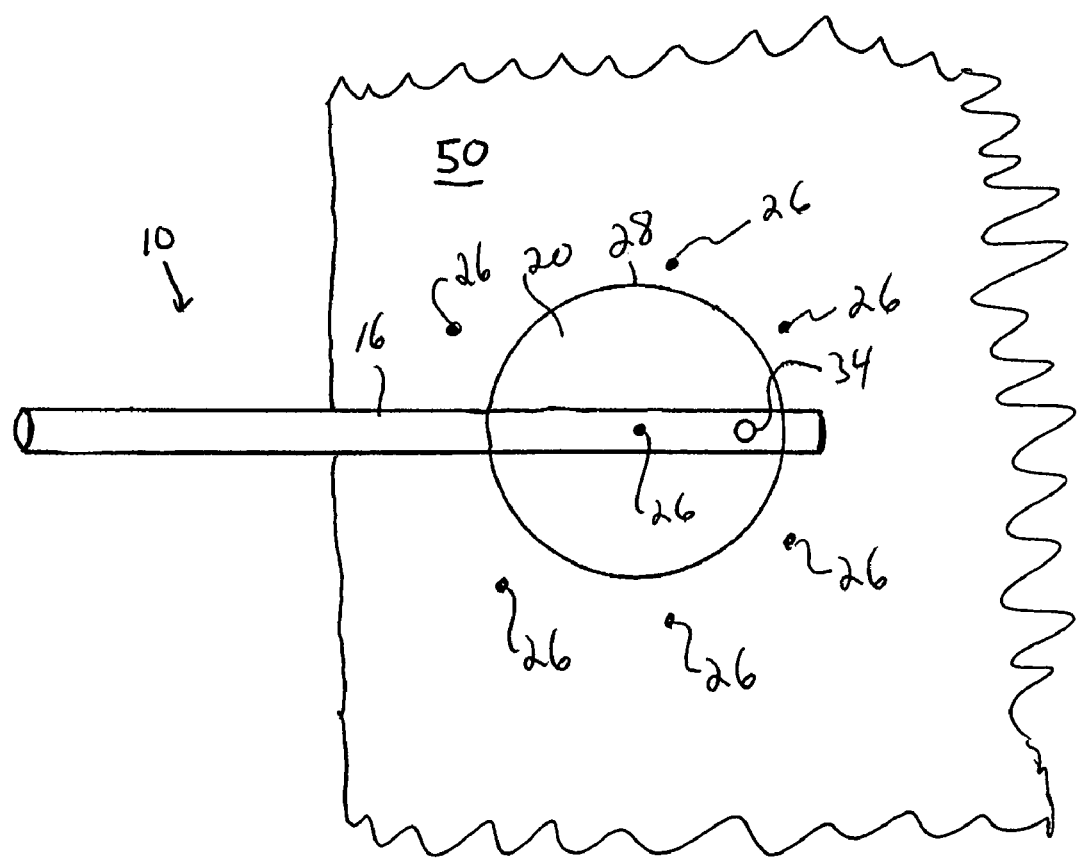

IMPLANTABLE RADIOTHERAPY/BRACHYTHERAPY RADIATION DETECTING APPARATUS AND METHODS

BACKGROUND OF THE INVENTION

The invention relates generally to apparatus and methods for use in treating proliferative tissue disorders, and more particularly to apparatus and methods for the treatment of such disorders by delivering radiation with a brachytherapy device that also measures treatment characteristics.

Malignant tumors are often treated by surgical resection of the tumor to remove as much of the tumor as possible. Infiltration of the tumor cells into normal tissue surrounding the tumor, however, can limit the therapeutic value of surgical resection because the infiltration can be difficult or impossible to treat surgically. Radiation therapy can be used to supplement surgical resection by targeting the residual malignant cells after resection, with the goal of sterilizing them, reducing the rate of recurrence or delaying the time to recurrence. Radiation therapy can be administered through one of several methods, or a combination of methods, including permanent or temporary interstitial brachytherapy, and external-beam radiation.

Brachytherapy refers to radiation therapy delivered by a spatially confined source of therapeutic rays inserted into the body at or near a tumor or other proliferative tissue disease site. For example, brachytherapy can be performed by implanting radiation sources directly into the tissue to be treated. Brachytherapy is most appropriate where 1) malignant tumor regrowth occurs locally, within 2 or 3 cm of the original boundary of the primary tumor site; 2) radiation therapy is a proven treatment for controlling the growth of the malignant tumor; and 3) there is a radiation dose-response relationship for the malignant tumor, but the dose that can be given safely with conventional external beam radiotherapy is limited by the tolerance or normal tissue. In brachytherapy, radiation doses are highest in close proximity to the radiotherapeutic source, providing a high tumor dose while sparing surrounding normal tissue. Brachytherapy is useful for treating malignant brain and breast tumors, among others.

Prior art brachytherapy devices have provided a number of advancements in the delivery of radiation to target tissue. For example, Winkler U.S. Pat. No. 6,413,204 describes a brachytherapy method and apparatus for treating tissue surrounding a surgically excised tumor with radioactive emissions to kill cancer cells that may be present in the tissue surrounding the excised tumor. The radiation is delivered in a predetermined dose range defined as being between a minimum prescribed absorbed dose for delivering therapeutic effects to tissue that may include cancer cells, and a maximum prescribed absorbed dose above which healthy tissue necrosis may result. The resulting treatment helps to prevent over-exposure to tissue at or near the brachytherapy device, while still delivering the minimum prescribed dose at the maximum prescribed distance from the device.

While such advancements have improved the treatment of proliferative tissue diseases, some challenges remain. Currently, the desired radiation dose is calculated based on the characteristics of the brachytherapy applicator (device), the radiation source and the surrounding tissue, yet the actual dose delivered is not tested to assure that over and/or under treatment do not occur. For example, if the radiation source is a radioactive seed positioned in the center of an expanded balloon, the calculated dose is based on the central positioning of the radiation source. If for some reason the radioactive seed was positioned off center, prior art brachytherapy devices do not have the means to determine that this harmful situation has or is occurring. Prior art brachytherapy devices also lack the ability to directly sense the surrounding tissue and determine the effectiveness of the proliferative tissue disorder treatment.

SUMMARY OF THE INVENTION

The present invention provides brachytherapy apparatus and methods for delivering and monitoring radioactive emissions to an internal body location. The device includes a catheter body member having a proximal end, a distal end, and an outer spatial volume disposed proximate to the distal end of the body member. A radiation source is preferably positioned in the outer spatial volume, and a treatment feedback sensor is disposed on the device.

In one embodiment, the treatment feedback sensor is a radiation sensor which can detect radiation emitted by the radiation source. The radiation sensor preferably produces data useful for determining if the delivered radiation dose was within the prescribed range. The data can also preferably be used to determine if the desired radiation profile was delivered to the surrounding tissue. In another aspect of the invention, the treatment feedback sensor is capable of detecting tissue temperature, oxygenation, pH, treatment agent concentration, cytokine concentration, or other characteristics related to radiation treatment.

In one embodiment, the treatment feedback sensor is positioned within the catheter body member. Other locations where the sensor may preferably be located include disposed on an expandable surface member which defines the outer spatial volume, or outside the device.

In another embodiment, the present invention includes a radiation therapy apparatus for delivering and monitoring radioactive emissions to a resected tumor cavity. The apparatus includes a catheter body member with proximal and distal ends, an expandable surface member disposed proximate to the distal end of the catheter body, a treatment feedback sensor, and an external radiation source positioned outside the tissue cavity for delivering radiation to target tissue surrounding the tissue cavity. The expandable surface member can be positioned within a resected tissue cavity and expanded to position the surrounding tissue such that the delivery of a radiation beam from the external radiation source is accurately delivered and measured by the treatment feedback sensor positioned within the tissue cavity.

In another embodiment, the invention includes the method of delivering and monitoring radioactive emissions to an internal body location. The method includes inserting a brachytherapy device into a resected cavity, the brachytherapy device including a catheter body member with proximal and distal ends, and an expandable surface member disposed proximate to the distal end of the catheter body member. A radiation source is preferably disposed within the expandable surface member. The method further includes inserting a radiation sensor into the resected cavity and delivering a minimum prescribed absorbed radiation dose to a target tissue, the target tissue being defined between the expandable surface member and a minimum distance outward from the expandable surface member. The radiation sensor senses the delivered radiation dose and data output from the sensor confirms that the brachytherapy device delivers the minimum prescribed dose.

In another embodiment, the present invention includes a brachytherapy apparatus for delivering and monitoring radioactive emissions to an internal body location. The apparatus includes a catheter body member having a proximal end, a distal end, and an outer spatial volume disposed proximate to the distal end of the body member. A radiation source is disposed in the outer spatial volume and a treatment feedback sensor is provided on the device. The treatment feedback sensor can be used to evaluate the treatment of proliferative tissue disorders.

BRIEF DESCRIPTION OF THE DRAWINGS

The invention will be more fully understood from the following detailed description taken in conjunction with the accompanying drawings:

FIG. 5 illustrates another embodiment of the brachytherapy device of the present invention shown in full view.

DETAILED DESCRIPTION OF THE INVENTION

Figure 1:
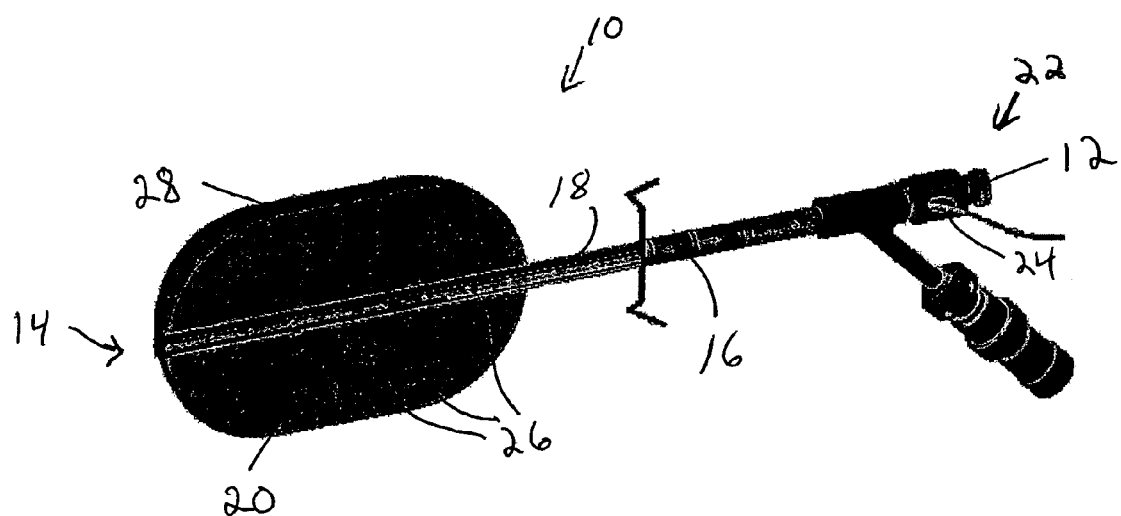
FIG. 1 illustrates the device of the present invention including a sectioned view of the outer spatial volume showing radiation sensors positioned therein.

The present invention provides interstitial brachytherapy devices that can deliver radioactive emissions used to treat proliferative tissue disorders and detect treatment characteristics to monitor the treatment regimen. The devices include a catheter body member with a proximal end, a distal end, and a inner lumen. An outer spatial volume is disposed proximate to the distal end of the body member with a radiation source preferably disposed therein. A treatment feedback sensor is disposed on the device.

Brachytherapy devices treat proliferative tissue disorders, such as cancerous tumors, by delivering radiation to the target area which contains both cancerous cells and healthy tissue. The radiation destroys the more radiosensitive cells, e.g. cancer cells, while hopefully minimizing damage to the surrounding healthy tissue. The most effective treatment delivers a dose above a minimum radiation dose necessary to destroy the proliferative tissue and below a maximum radiation dose to limit damage to healthy tissue. In addition to delivering a radiation dose within the proper range, brachytherapy devices may also deliver the radiation in a desired pattern. For example, it may be desirable to deliver radiation in a uniform three dimensional profile.

In use, the desired radiation dose is calculated based on factors such as the position of the radiation source, the type of radiation used, and the characteristics of the tissue and brachytherapy device. The brachytherapy device is then positioned within a tissue cavity and the dose is delivered. Unfortunately, variations in the brachytherapy device, in the surrounding tissue, or in the positioning of the radiation source can effect the delivered dose. For example, in some cases the radiation source is loaded into the brachytherapy device after the device has been positioned within the tissue cavity, but if the radiation source is improperly positioned during the loading process the surrounding tissue may not receive the desired treatment. The present invention overcomes these difficulties by positioning a treatment feedback sensor on the brachytherapy device. In one embodiment, the treatment feedback sensor is a radiation sensor that can monitor the delivered dose and assure that the prescribed radiation dose is delivered to the correct tissue. In addition, data from the radiation sensor allows the dose to be modified based on feedback from an initial radiotherapy/brachytherapy fraction.

In addition to detecting radiation, or as an alternative, the treatment feedback sensor can detect other characteristics related to treatment of proliferative tissue disorders. For example, the treatment feedback sensor could detect changes in tissue caused by radiation treatment including changes in tissue temperature, oxygenation, pH, and cytokine concentration. By monitoring such characteristics, the effectiveness of the treatment can be analyzed. In addition, radiation treatment can be combined with other supplemental treatments such tissue heating and/or delivery of a treatment agent (e.g., a chemotherapy drug). The treatment feedback sensor can be used to monitor supplemental treatment regimens. For example, the sensors can be used to detect the delivery of a treatment agent, e.g., the flux of a chemotherapy drug being delivered to surrounding tissue, or to detect changes in tissue caused by the supplemental treatment, e.g., changes in tissue temperature.

FIG. 1 depicts one embodiment of brachytherapy device 10 of the present invention including catheter body member 16 having proximal end 12, distal end 14, and inner lumen 18. Outer spatial volume 20 is preferably disposed on the distal portion of catheter body member 16. The proximal end of catheter body 16 preferably includes a handle portion 22 for manipulating the device, and a port 24 which opens to inner lumen 18. At least one treatment feedback sensor 26 is positioned on the device, and may be disposed within catheter body member 16 as shown in FIG. 1. In addition a radiation source (not shown) is preferably positioned within outer spatial volume 20.

Figure 2:
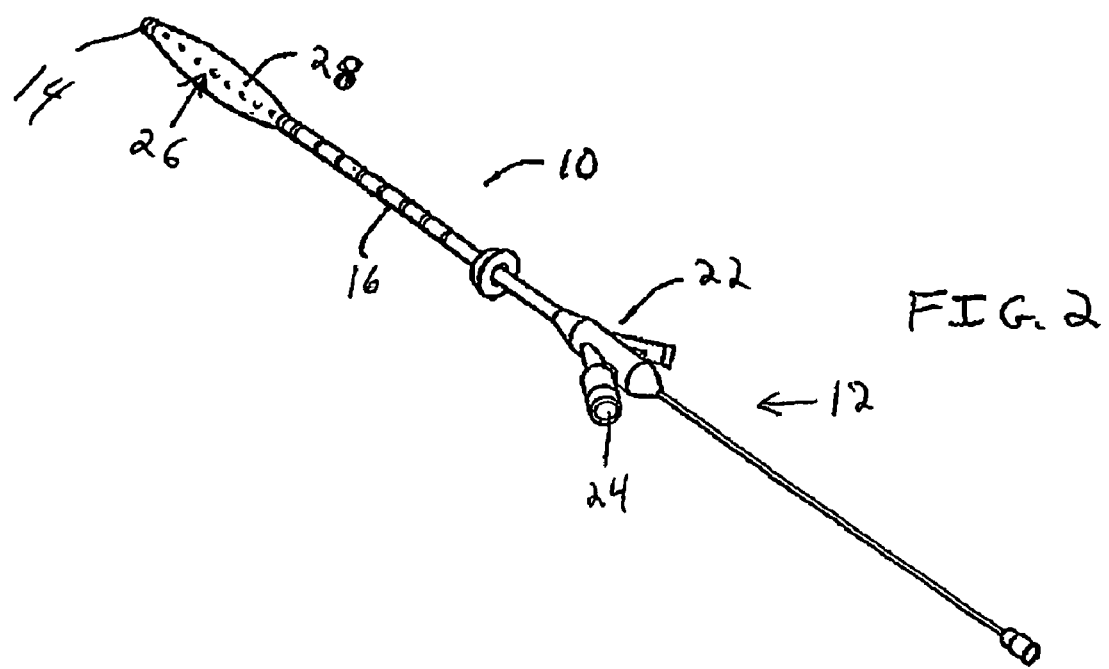
FIG. 2 illustrates another embodiment of the brachytherapy device of the present invention shown in perspective.

Outer spatial volume 20 is preferably defined by an expandable surface member 28 which can be used to position tissue, provide spacing between the radiation source and the adjacent tissue, and/or supply containment for radiation source materials. In addition, sensor 26 (or sensors 26) can be positioned on expandable surface member 28 as shown in FIG. 2. A person of skill in the art will appreciate that positioning sensor 26 on the expandable surface member could include positioning on the inner or outer surface of expandable surface member 28, as well as, positioning the sensor within the wall of expandable surface member 28.

In one embodiment, the treatment feedback sensor positioned on the expandable surface member can sense radiation ("radiation sensor"). A radiation sensor may be preferable for providing an accurate view of the strength of the radiation as it leaves the device. Other types of sensors can also be placed on the expandable surface member to detect the effect of radiation on surrounding tissue. The sensor may also have the ability to sense other treatment characteristics of the tissue in contact with the expandable surface member.

A variety of expandable surface members can be used with the present invention, and in one embodiment expandable surface member 28 is an inflatable balloon. It will be understood that the term "balloon" is intended to include distensible devices which can be, but need not be, constructed of elastic material. Exemplary balloons include the variety of distensible devices designed for use with surgical catheters. In use, the balloon can be expanded by injecting an inflation material though catheter body member 16 and into the balloon by way of an inflation port 34 in the catheter body member.

In one embodiment, the balloon is constructed of a solid material that is substantially impermeable to active components of a treatment fluid (e.g. radiation source material) with which it can be filled, and is also impermeable to body fluids, e.g., blood, cerebrospinal fluid, and the like. An impermeable balloon is useful in conjunction with a radioactive treatment fluid to prevent the radioactive material from escaping the treatment device and contaminating the surgical field or tissues of the patient.

In another embodiment, the balloon is permeable to a treatment agent, and permits a treatment agent to pass out of device 10 and into a body lumen, body cavity, or the anatomical site of the device location. A permeable balloon is useful when the treatment agent is a drug such as for example, a chemotherapeutic drug which must contact tissue to be effective. U.S. Pat. No.: 6,537,194 to Winkler and U.S. Pat. No. 5,931,774 to Williams et al. disclose exemplary permeable balloons and treatment substances and are hereby incorporated by reference in their entirety. The treatment feedback sensor can be used to monitor the passage of treatment agent out of the permeable balloon. For example, treatment feedback sensor 26 could be positioned on the balloon to measure treatment agent concentration. An additional sensor could also be positioned in or on tissue surrounding device 10 to detect the concentration of treatment agent.

By positioning treatment feedback sensors on the device, a user can monitor the delivery of a treatment material from the device to surrounding tissue. The sensor could be used to find information on the rate of delivery, the extent of delivery, the uniformity of delivery, and other dosing information. Such a sensor can be particularly advantageous because they can overcome the difficulty of determining how much treatment agent is being delivered and to where it is being delivered. Presently, the delivery rate of treatment agent is determined indirectly by measuring factors such as the pressure applied to the fluid and/or the change in volume of the fluid. The treatment feedback sensors of the present invention allow for direct measurement of the treatment agent as it leaves the device.

A treatment agent can also be delivered from the surface of the balloon to the surrounding tissue. U.S. patent application entitled DRUG ELUTING BRACHYTHERAPY METHODS AND APPARATUS, discloses such devices and is hereby incorporated by reference in its entirety. A treatment feedback sensor can be used to detect the delivery of a treatment agent from the surface of the balloon to the surrounding tissue. A sensor positioned in a layer of treatment material positioned on the outer surface can preferably sense how much of the treatment agent has been delivered and/or how much remains. Sensor are useful for determining when the treatment agent is fully delivered. Where multiple treatment agents are layered on the outer surface of the balloon, the sensor is also useful for sensing which treatment agent is being delivered. The sensor could also be useful for detecting the level of treatment agent in the adjacent tissue.

Figure 3:
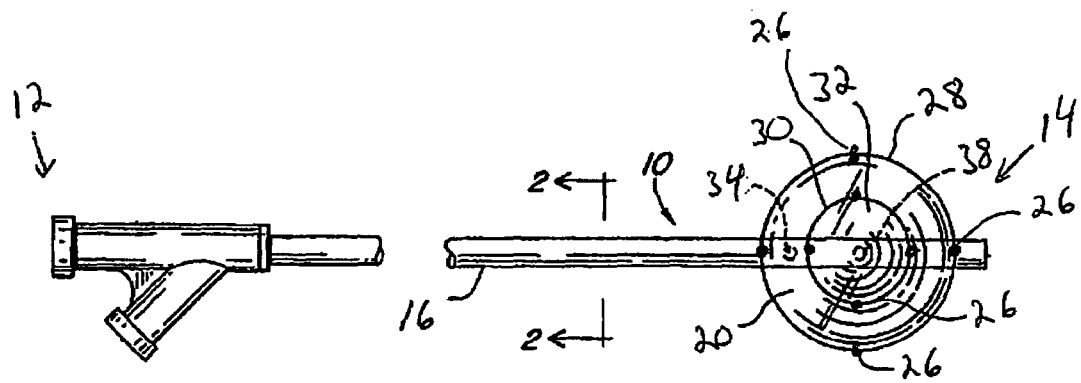
FIG. 3 illustrates another embodiment of the brachytherapy device of the present invention shown in full view.
Figure 3A:
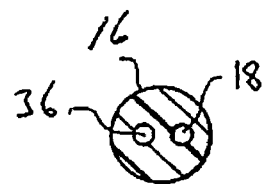
FIG. 3A illustrates a cross sectional view of the device pictured in FIG. 3.

The invention also contemplates the use of multiple balloons, e.g., a double-walled structure as shown in FIG. 3. Such a balloon can comprise, for example, an inner balloon 30 containing an inner spatial volume 32 being positioned within an outer balloon 28, and the outer balloon defining the outer spatial volume 20 as the space between the inner wall and the outer wall. Outer spatial volume 20 is preferably in fluid communication with first inner lumen 18 through first inflation port 34, while inner spatial volume 32 is preferably in fluid communication with a second inner lumen 36 via second inflation port 38. First and second inner lumens 18, 36 are shown by the cross sectional view of catheter body member 16 in FIG. 3A.

A double walled balloon (or even a higher order balloon, e.g. triple walled) provides more options for controlling and direction radiation dosing. For example, a double walled balloon can provide spacing between a radiation source and adjacent tissue so that more powerful radiation sources can be used (See, e.g., U.S. Pat. No. 5,913,813 to Williams et al. and U.S. Pat. No. 6,413,204 to Winkler et al. which are hereby incorporated by reference in their entirety.). While "hotter" radiation sources allow delivery of absorbed doses deeper into the target tissue and reduce the risk of healthy tissue necrosis, proper spacing and positioning of the radiation source are important. Sensor 26 of the present invention can therefore provide useful feedback to assure the balloons walls and the radiation source are appropriately configured. In particular, a radiation-sensing treatment feedback sensor can be used to detect radiation levels and determine if any area is receiving too much or too little radiation. Other sensors could also be used to indirectly determine proper spacing and positioning by monitoring characteristics such as tissue temperature.

In some applications, the brachytherapy device 10 is designed to provide a dosing profile consistent with the shape of the outer spatial volume. That is, the absorbed dose within the target tissue at points equidistant from the surface of the outer spatial volume should be substantially uniform in substantially every direction creating three dimensional isodose profiles substantially similar in shape to the outer spatial volume. In addition, the expandable surface member of the outer spatial volume may be sufficiently firm so as to force the target tissue to take on the shape of the expandable surface member. With the tissue thus shaped, the surrounding tissue receives a uniform dose of radiation.

Treatment feedback sensors positioned on the device of the present invention can be used to confirm that a three dimensional isodose profile is generated and delivered to the surrounding tissue. The sensors may be particularly useful where the expanded surface member is used to shape the tissue cavity walls. Although imaging techniques can confirm the relative position of the tissue cavity and the brachytherapy device, treatment feedback sensors can provide actual dosing information to assure the tissue and the device do not shift during the procedure. Although the sensors can be positioned anywhere on the device, in may be desirable to position radiation-sensing treatment feedback sensors on the expandable surface member as shown in FIG. 3 to directly test the radiation levels leaving the surface of the device (e.g. all the radiation sensor readings should be roughly equal).

In an alternative embodiment, it may be desirable to deliver an asymmetric radiation dose to protect radiation-sensitive tissue. Two possible arrangements for delivering an asymmetric dose include radiation shielding and/or positioning the radiation source in an asymmetric configuration as described in U.S. Pat. No. 6,482,142 to Winkler et al. which is incorporated herein by reference in its entirety. For example, shielding can be accomplished when all or a portion of the expandable surface member is formed from, or coated with, a radio-opaque material. An asymmetric isodose profile can also be created by the relative position of the radiation source or sources to one another and to the outer spatial volume.

Delivering an asymmetric dose provides an additional challenge because the radiation dose is focused on one region and shielded from another. If the device is improperly positioned within the tissue cavity or if the radiation profile has an unexpected shape, sensitive tissue could be damaged. Treatment feedback sensors can therefore help to protect radiation-sensitive tissue by confirming proper shielding and proper positioning of device 10. Although sensors may be located anywhere on the device to provide dosing information, sensors positioned toward the exterior or outside of device 10 can provide valuable data regarding the amount of radiation reaching sensitive tissue. In one embodiment, a radiation-sensing treatment feedback sensor can be positioned on the wall of a tissue cavity in the area which needs shielding.

The radiation source of the present invention preferably includes any radiation source which can deliver radiation to treat proliferative tissue disorders. Exemplary radiation sources include high dose brachytherapy radiation, medium dose brachytherapy radiation, low dose brachytherapy radiation, pulsed dose rate brachytherapy radiation, external beam radiation, and combinations thereof. Although the device of the present invention is described with reference to radiation sources positioned within the device, possible radiation sources can include external radiation sources positioned outside the device or patient's body such as IMTR, 3-D conformal therapy, orthovolatage, stereotactic radiation, and combinations thereof.

In one embodiment, device 10 treats proliferative tissue disorders by using the expandable surface member to position and/or stabilize tissue surrounding the tissue cavity and then deliver radiation from a source external to the tissue cavity. U.S. patent application entitled TISSUE POSITIONING SYSTEMS AND METHODS FOR USE WITH RADIATION THERAPY, discloses such devices and is hereby incorporated by reference in its entirety. Treatment feedback sensors positioned on the device can provide feedback to ensure the prescribed dose is delivered to the positioned tissue.

The radiation source can also be positioned within brachytherapy device 10, and even more preferably, can be positioned within outer spatial volume 20. In particular, the radiation source may be disposed within inner spatial volume 32 inside outer spatial volume 20, e.g. inside an inner balloon as shown in FIG. 3. The radiation source can include a predetermined radionuclide, for example, I-125, I-131, Yb-169 or other sources of radiation, such as radionuclides that emit photons, beta particles, gamma radiation, or other therapeutic rays including x-ray radiation (e.g., manmade radiation sources such as miniature x-ray generators or linear accelerators). The radioactive material contained within the outer spatial volume can be a fluid made from any solution of radionuclides(s), e.g., a solution of I-125 or I-131. A radioactive fluid can also be produced using a slurry of suitable fluid containing small particles of solid radionuclides, such as Au-198, Y-90. Moreover, the radionuclides (ds) can be embodied in a gel. A person of skill in the art will appreciate that various radiation sources can be used with the brachytherapy device of the present invention.

Figure 4:
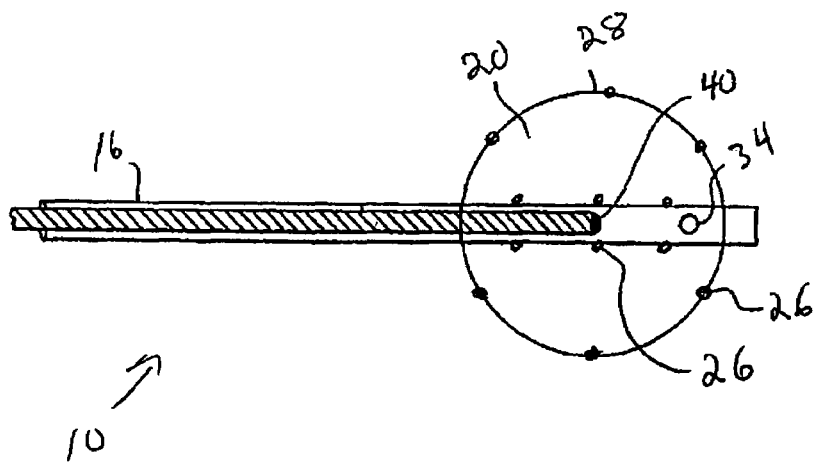
FIG. 4 illustrates another embodiment of the brachytherapy device of the present invention shown in full view.

In another embodiment, the radiation source may be a solid spherical radiation emitting material 40 positioned within catheter body member 16 as shown in FIG. 4. For example, radioactive micro spheres of the type available from the 3M Company of St. Paul, Minn., may be used. This radioactive source can either be preloaded into the catheter body member at the time of manufacture or loaded into the device after it has been implanted into the space formerly occupied by the excised tumor. The solid radiation emitting material 40 can be inserted through catheter 16 on a wire 42, for example, using an afterloader (not shown). Such a solid radioactive core configuration offers an advantage in that it allows a wider range of radionuclides than if one is limited to liquids. Solid radionuclides that could be used with the device of the present invention are currently generally available as brachytherapy radiation sources.

Treatment feedback sensors can provide valuable information regarding the characteristics of the radiation source. For example, a radiation-sensing sensor can be used to provide data on the location of the radiation source material after it is loaded into the device. This data can then be used to calculate the radiation dose and/or to alert users if the radiation source material is improperly loaded. Useful radiation sensors can be positioned anywhere on the device including on catheter body member 16 and expandable surface member 28. In one embodiment, a radiation sensor (or sensors) is positioned on the catheter body to detect when the radiation source material is properly positioned. For example, as shown in FIG. 4, sensors may be positioned at the point on the catheter body member where it is desired to position the radiation emitting material 40. When the sensor reaches its maximum radiation reading the user will know the radiation emitting material is properly positioned.

Catheter body member 16 of device 10 provides a means for positioning outer spatial volume 20 within the resected tissue cavity and presents a path for delivering radiation source material and inflation material (if used). Although the exemplary catheter body members illustrated in the FIGS. have a tubular construction, one of skill in the art will appreciate that catheter body member 16 can have a variety of shapes and sizes. Catheter body members suitable for use in the invention can include catheters which are known in the art. Although catheter body member 16 can be constructed from a variety of materials, in one embodiment the catheter body member material is silicone, preferably a silicone that is at least partially radio-opaque, thus facilitating x-ray localization of catheter body member 16 after insertion of device 10. Catheter body member 16 can also include conventional adapters for attachment to a treatment fluid receptacle and the balloon, as well as devices, e.g., right-angle devices, for conforming catheter body member 16 to contours of the patient's body.

As shown in FIG. 1, treatment feedback sensors 26 can be positioned within catheter body member 16 to provide information on the proliferative tissue disorder treatment being delivered to the patient. The sensor or sensors can be positioned inside any inner lumen (e.g. first inner lumen 18) of catheter body member 16. Alternatively, sensor(s) 26 could be positioned within the wall of catheter body member 16 or on the outside of the catheter body member. Multiple sensors 26, as shown in FIG. 1, may be preferable to improve accuracy and provide a more detailed picture of the therapy. In one embodiment, a string of spaced apart radiation-sensing sensors 26 can provide data from points along the whole length of brachytherapy device 10. Preferably, sensors 26 are positioned at intervals of about 1 cm.

Treatment feedback sensor 26 used with the device of the present invention preferably includes radiation sensors capable of detecting and/or measuring radiation delivered by brachytherapy devices or external beam radiotherapy. Exemplary radiation includes penetrating emissions such as gamma rays, x-rays, and non-penetrating emissions such as beta particles (negative and positive), alpha particles, protons and combinations thereof. Preferably, the radiation sensors are capable of measuring radiation over a range of about 1.0 Gy to 400 Gy. An exemplary radiation sensor can include MOSFET, diode dosimeters, ionization chambers, thermoluminescent dosimeters and combinations thereof. The radiation sensor should preferably be small enough to be positioned on the brachytherapy device. For example, the sensor may be in the range of about 0.01 mm to 3.0 cm in the longest dimension. Preferred sizes for individual sensors is 1 mm by 1 mm by 3 mm or smaller in any or all of those dimensions.

In addition to the ability to sense radiation, or as an alternative, the treatment feedback sensor 26 can preferably detect other physical properties such as temperature, oxygenation of tissue, pH, drug concentration, cytokine concentration, and/or other tissue properties.

Treatment feedback sensor 26 can be disposed on brachytherapy device 10 in a variety of ways including fixing the sensor to the device. By mating the sensor with the device, the location of the device is know and the sensor and brachytherapy device can be inserted in one step. A person of skill in the art will appreciate that the sensor can be fixed to the device in a variety of ways, including but not limited to, adhesion, embedding within the brachytherapy device, insert molding, surface deposition, ultrasonic welding and beading.

In an alternative embodiment treatment feedback sensor 26 can be nonpermanently disposed on brachytherapy device 10. For example, the sensor can be in contact with the device, but not mated thereto. Nonmating contact allows sensor 26 to be inserted into a tissue cavity separately from brachytherapy device 10. In one embodiment, the sensor can be inserted into a tissue cavity and then the brachytherapy device can be inserted and expanded. Expansion of the brachytherapy device can then hold the sensor in position during therapy. Alternatively, sensor 26 can be disposed within device 10 by insertion into catheter body member 16 before or after insertion of the brachytherapy device into the tissue cavity.

In yet a further embodiment, an additional sensor(s) can be positioned around the outside of device 10. FIG. 5 shows sensors 26 positioned in tissue 50 surrounding the resected tissue cavity. By positioning sensors outside the device, as well as on the device, the characteristics of the tissue a distance from the device can be determined. For example, it is expected that the radiation level drops as a function of distance from the radiation source, and sensors positioned in the surrounding tissue area can confirm that the radiation drops to the expected level. In addition, sensors positioned in tissue beyond the target tissue area can be used to confirm a minimal dose (or no dose) is delivered to healthy tissue. Such sensors may also have the capability to sense other treatment characteristics such as temperature and treatment agent concentration.

Along with data received from treatment feedback sensor 26, additional information such as the sensor's location helps to determine the profile of the radiation dose. While sensor 26 may be positioned in a predetermined location, the location can also be determined in vivo. For example, the treatment feedback sensor may preferably be visible to a medical imaging modality such as, radiotherapy (e.g. x-rays, fluoroscopy), computed tomography, magnetic resonance imaging, and ultrasound. In one embodiment, the brachytherapy device is inserted into the tissue cavity and then the device and/or sensor is imaged to determine the location of the device and the sensor. Other means for determining the position of the device, the sensor and/or target tissue include fiducial markers. Fiducial markers may be markers positioned on the device, and may include anatomical landmarks in the body, and/or implanted foreign bodies such as radioopaque markers or surgical clips.

The treatment feedback sensor preferably communicates with an external device that displays, processes, and/or records the radiation dose. Communication between the sensor and the external device can be made via direct physical connection (via wires or fiber that transmit the signals) or via wireless interface that communicates the signal without benefit of cabling.

The present invention also includes the method of using the brachytherapy device to treat target tissue and sense radioactive emissions. The interstitial brachytherapy apparatus of the invention can be used in the treatment of a variety of malignant tumors, and is especially useful in the treatment of brain and breast tumors. Treatment feedback sensor 26 can monitor the treatment and help to ensure the prescribed successful treatment of the surrounding tissue.

Many breast cancer patients are candidates for breast conservation surgery, also known as lumpectomy, a procedure that is generally performed on early stage, smaller tumors. Breast conservation surgery is typically followed by postoperative radiation therapy. Studies report that 80% of breast cancer recurrences after conservation surgery occur near the original tumor site, strongly suggesting that a tumor bed "boost" of local radiation to administer a strong direct dose may be effective in killing any remaining cancer and preventing recurrence at the original site. Numerous studies and clinical trials have established equivalence of survival for appropriate patients treated with conservation surgery plus radiation therapy compared to mastectomy.

Surgery and radiation therapy are the standard treatments for malignant solid brain tumors. The goal of surgery is to remove as much of the tumor as possible without damaging vital brain tissue. The ability to remove the entire malignant tumor is limited by its tendency to infiltrate adjacent normal tissue. Partial removal reduces the amount of tumor to be treated by radiation therapy and, under some circumstances, helps to relieve symptoms by reducing pressure on the brain.

A method according to the invention for treating these and other malignancies begins by surgical resection of a tumor site to remove at least a portion of the cancerous tumor and creation of a resection cavity. Following tumor resection the surgeon places an interstitial brachytherapy device, having an outer spatial volume as described above, into the tissue cavity. The outer spatial volume, preferably being defined by an expandable surface member, is expanded and the prescribed dose of radiotherapy is delivered. This treatment may be repeated over the course of a treatment regimen.

In one embodiment, treatment feedback sensors positioned on the device sense the radiation delivered by the radiation source(s) during radiation dosing. The radiation sensors can deliver data during irradiation (e.g., real-time measurements), after each fraction of radiotherapy/brachytherapy, and/or upon completion of the entire course of radiotherapy/brachytherapy. The data is preferably collected by a computer and can be used to verify the delivered radiation dose. The verification step confirms that the radiation dose is delivered to the correct area and/or is within the prescribed limits.

A feedback step can also be useful for modifying future radiation doses (or fractions) to improve the distributed radiation profile. In particular, sensor 26 can detect the radioactive emissions and delivers data regarding the radiation levels detected. In one embodiment, a radiation source emits a first dose of radiation which is detected by the sensor positioned on the device. The first dose can be any dose smaller than the full prescribed dose. Data collected from the first dose is then used to evaluate the dosing profile and dosing intensity, and any errors can be fixed prior to delivering the full dose.

In another embodiment, the treatment feedback sensors can be used to evaluate the treatment procedure. The sensors can collect data used to determine if the residual malignant cells are being destroyed and to evaluate damage to healthy tissue. By sensing physical characteristics of the surrounding tissue such as, for example oxygenation, pH, temperature, and cytokine concentration, a user can determine how the delivered dose effected the surrounding tissue. In some cases, different regions of tissue or different patients may required different doses of radiation. By using treatment feedback sensors to directly sense the surrounding tissue, the device of the present invention can help to ensure effective treatment.

In yet another embodiment, the treatment feedback sensor can sense the delivery of a supplemental treatment such as tissue heating or the delivery of a treatment agent. Sensors positioned on the device can be used monitor the supplemental treatment and determine its effectiveness.

A person skilled in the art will appreciate that the foregoing is only illustrative of the principles of the invention, and that various modifications can be made by those skilled in the art without departing from the scope and spirit of the invention. All references cited herein are expressly incorporated by reference in their entirety.

The invention claimed is:

1. A brachytherapy apparatus for delivering and monitoring radioactive emissions to an internal body location, comprising:
    a catheter body member having a proximal end, a distal end, and an outer spatial volume disposed proximate to the distal end of the body member;
    a radiation source disposed in the outer spatial volume;
    a radiation sensor provided on the device; and
    an additional radiation sensor is positioned outside the brachytherapy device;
    wherein the radiation sensors measures the radiation delivered from the radiation source.

2. The apparatus of claim 1, wherein the radiation sensor provided on the device is positioned within the catheter body member.

3. The apparatus of claim 2, wherein the radiation sensor is positioned in the center of the outer spatial volume.

4. The apparatus of claim 1, wherein the radiation sensor provided on the device is positioned within the outer spatial volume.

5. The apparatus of claim 1, wherein the outer spatial volume is defined by an expandable surface member and the radiation sensor provided on the device is mated with the expandable surface.

6. The apparatus of claim 1, wherein the outer spatial volume is defined by an expandable surface member.

7. The apparatus of claim 6, wherein the radiation source generates a three-dimensional isodose profile that is substantially similar in shape to the expandable surface member.

8. The apparatus of claim 7, wherein output from the sensors is used to verify that a three-dimensional isodose profile substantially similar in shape to the expandable surface member is delivered to adjacent tissue.

9. The apparatus of claim 7, wherein the radiation sensor provided on the device is mated with the expandable surface member.

10. The apparatus of claim 1, wherein the brachytherapy device generates an asymmetric isodose radiation profile.

11. The apparatus of claim 1, wherein an inner spatial volume is disposed within the outer spatial volume.

12. The apparatus of claim 11, wherein the radiation source is disposed within the inner spatial volume.

13. The apparatus of claim 12, wherein the inner and outer spatial volumes are defined by inner and outer balloons.

14. The apparatus of claim 13, wherein at least one radiation sensor is positioned on the inner and the outer balloon.

15. The apparatus of claim 1, wherein the radiation source is a solid radiation source.

16. The apparatus of claim 15, wherein the radiation sensor provided on the device is positioned on the catheter body member at a position in the longitudinal direction where it is desired to position the radiation source.

17. The apparatus of claim 1, wherein the brachytherapy apparatus is an interstitial brachytherapy apparatus.

18. The apparatus of claim 1, wherein more than two radiation sensors are provided.

19. The apparatus of claim 18, wherein the additional radiation sensor is configured to be positioned in tissue adjacent to the device.

20. The apparatus of claim 18, wherein the additional radiation sensor is configured to be positioned on the wall of the resected tissue cavity.

21. A brachytherapy apparatus for delivering radioactive emissions to an internal body location, comprising:
    a catheter body member having a proximal end, a distal end, and an outer spatial volume disposed proximate to the distal end of the body member;
    a radiation source disposed in the outer spatial volume;
    a treatment feedback sensor provided on the device; and
    an additional treatment feedback sensor is positioned outside the brachytherapy apparatus;
    wherein the treatment feedback sensors can be used to evaluate the treatment of proliferative tissue disorders.

22. The apparatus of claim 21, wherein the treatment feedback sensors measures the radiation delivered from the radiation source.

23. The apparatus of claim 22, wherein the treatment feedback sensors detects the delivery of a supplemental treatment.

24. The apparatus of claim 23, wherein the treatment feedback sensors monitors the delivery of a treatment agent to the surrounding tissue.

25. The apparatus of claim 22, wherein the treatment feedback sensors measures one of the characteristics selected from the group consisting of, tissue temperature, oxygenation, pH, treatment agent concentration, and cytokine concentration.

26. The apparatus of claim 25, wherein the outer spatial volume is defined by a permeable balloon and the treatment feedback sensors detects a treatment agent which is capable of permeating through the wall of the permeable balloon.

27. The apparatus of claim 22, wherein the outer spatial volume is defined by an expandable surface member and the treatment feedback sensors are mated with the expandable surface.

28. The apparatus of claim 22, wherein the treatment feedback sensors are positioned within the catheter body member.

* * * * *